(12) United States Patent
McBride

(10) Patent No.: US 10,842,960 B2
(45) Date of Patent: *Nov. 24, 2020

(54) BREATHING GAS DELIVERY SYSTEM

(71) Applicant: MSafe, Inc., Long Beach, CA (US)

(72) Inventor: Robert McBride, Long Beach, CA (US)

(73) Assignee: MSAFE, INC., Long Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/741,119

(22) Filed: Jan. 13, 2020

(65) Prior Publication Data

US 2020/0155779 A1    May 21, 2020

Related U.S. Application Data

(63) Continuation of application No. 16/290,712, filed on Mar. 1, 2019, now Pat. No. 10,561,811.

(Continued)

(51) Int. Cl.
*A61M 16/00* (2006.01)
*A61M 16/10* (2006.01)
(Continued)

(52) U.S. Cl.
CPC ...... *A61M 16/022* (2017.08); *A61M 16/0003* (2014.02); *A61M 16/0816* (2013.01);
(Continued)

(58) Field of Classification Search
CPC .............. A61M 16/00; A61M 16/0003; A61M 16/0078; A61M 16/0087; A61M 16/01; A61M 16/06; A61M 16/0605; A61M 16/0611; A61M 16/0616; A61M 16/0627; A61M 16/0666; A61M 16/0672; A61M 16/0816; A61M 16/0833; A61M 16/104; A61M 16/106; A61M 16/20; A61M 16/201; A61M 2205/84; A61B 7/00; A61B 7/02;
(Continued)

(56) References Cited

U.S. PATENT DOCUMENTS

| 2,208,633 | A |   | 7/1940 | Heidbrink |   |
| 3,556,097 | A | * | 1/1971 | Wallace | A61M 16/06 128/202.23 |
| 3,721,238 | A | * | 3/1973 | Wise | A61M 16/104 128/205.28 |
| 3,815,596 | A |   | 6/1974 | Keener |   |

(Continued)

OTHER PUBLICATIONS

Pentair, Oxygen Manifolds, https://smhttp-ssl-29106.nexcesscdn.net/media/docs/MFV3-MFV5-Product-Guide.pdf.

*Primary Examiner* — Joseph D. Boecker
(74) *Attorney, Agent, or Firm* — Cislo & Thomas, LLP; Katherine B. Sales

(57) ABSTRACT

A breathing gas delivery system comprising a gas flow controller, at least one breathing apparatus, and at least one first length of tubing coupling the breathing apparatus to the gas flow controller. The gas flow controller has a body having an on/off switch, at least one gas input, at least one gas output, and at least one control mechanism for controlling flow of gas to the gas output. The breathing apparatus comprises a T-shaped gas input, a breathing bag coupled to the T-shaped gas input, a second length of tubing having two opposed ends, wherein one end is coupled to the other arm of the T-shaped gas input, a filter coupled the second length of tubing, and a nasal assembly coupled to the filter.

13 Claims, 7 Drawing Sheets

Related U.S. Application Data

(60) Provisional application No. 62/637,665, filed on Mar. 2, 2018.

(51) Int. Cl.
*A61M 16/08* (2006.01)
*A61M 16/06* (2006.01)
*A62B 7/00* (2006.01)

(52) U.S. Cl.
CPC ....... *A61M 16/106* (2014.02); *A61M 16/0605* (2014.02); *A62B 7/00* (2013.01)

(58) Field of Classification Search
CPC .... A61B 7/12; A61B 7/14; A61B 9/02; A61B 9/04; A61B 17/04; A61B 18/00; A61B 18/003; A61B 18/006; A61B 18/02; A61B 18/025; B64D 2231/00; B64D 2231/02; B64D 2231/025
See application file for complete search history.

(56) References Cited

U.S. PATENT DOCUMENTS

| | | | |
|---|---|---|---|
| 4,034,753 A * | 7/1977 | Connel | A61M 16/104 |
| | | | 128/203.19 |
| 4,151,843 A | 5/1979 | Brekke | |
| 4,449,524 A | 5/1984 | Gray | |
| 4,905,684 A | 3/1990 | Heffer | |
| 5,924,419 A | 7/1999 | Kotliar | |
| 6,834,648 B2 | 12/2004 | Tokasz et al. | |
| 8,291,906 B2 | 10/2012 | Kooij et al. | |
| 8,584,674 B1 | 11/2013 | Poliard | |
| 10,561,811 B2 * | 2/2020 | McBride | A61M 16/0816 |
| 2003/0154982 A1 | 8/2003 | Tokasz | |
| 2006/0283451 A1 | 12/2006 | Albertelli | |
| 2009/0260631 A1 | 10/2009 | Aubonnet | |
| 2010/0132706 A1 * | 6/2010 | Nashed | A61M 16/0078 |
| | | | 128/203.28 |
| 2011/0083748 A1 | 12/2011 | Ellis | |
| 2015/0209541 A1 | 7/2015 | Harwood et al. | |
| 2015/0359988 A1 | 12/2015 | Humphries | |

* cited by examiner

BREATHING GAS DELIVERY SYSTEM

CROSS-REFERENCE TO RELATED APPLICATIONS

This application is a Continuation of U.S. patent application Ser. No. 16/290,712, filed Mar. 1, 2019, titled "Breathing Gas Delivery System," which claims priority to U.S. Patent Application No. 62/637,665, filed Mar. 2, 2018, titled "Breathing Gas Delivery System." The contents of both applications are incorporated herein by reference in their entirety.

BACKGROUND

Mercury is the most toxic, non-radioactive element on the planet. Elemental mercury is a component of "silver amalgam" teeth fillings. When these fillings are removed from teeth, large amounts of poisonous mercury vapor are released that can negatively affect the patient, doctor, staff and the environment Accordingly, there is a need for a breathing gas delivery system for simultaneous use by a doctor, an assistant, and a patient during removal of mercury fillings.

SUMMARY

In a first embodiment, the present invention is directed to a breathing gas delivery system comprising a gas flow controller, three breathing apparatuses, and three first lengths of tubing coupling the breathing apparatuses to the gas flow controller.

The gas flow controller comprises a body having an on/off switch coupled to the body for controlling breathing gas flow into the flow controller, a body passageway disposed through the body, at least one gas input disposed within the body, the gas input comprising a gas input passageway disposed there through, the gas input passageway being in fluid communication with the body passageway, three gas outputs disposed within the body, each gas output comprising a gas output passageway disposed there through, each gas output passageway being in fluid communication with the body passageway and the gas input passageway, and three control mechanisms disposed along the body, where each control mechanism corresponds to and controls one of the three gas outputs.

Each breathing apparatus comprises a T-shaped gas input having two arms coupled to and extending perpendicularly to a body, the body having a free end, a breathing bag coupled to the free end of the body of the T-shaped gas input, a second length of tubing having two opposed ends, wherein one end is coupled to the other arm of the T-shaped gas input, a filter containing at least one layer of material coupled to the other end of the second length of tubing, and a nasal assembly coupled to the filter.

In a second embodiment, the present invention is directed to a breathing gas delivery system comprising a gas flow controller and at least one breathing apparatus.

In a third embodiment, the present invention is directed to a kit for assembling a breathing gas delivery system.

Each first length of tubing has two opposed ends, wherein one end is coupled to a breathing apparatus and the other end is coupled a gas output.

The gas input passageway can have a longitudinal axis that is parallel to the longitudinal axis of the body.

Each of the gas outputs can have a longitudinal axis that is perpendicular to the longitudinal axis of the body.

The control mechanisms each comprise a dial coupled to a needle valve that extends into the body passageway and controls flow of gas to the corresponding gas output.

Optionally, each nasal assembly comprises a nasal hood.
Optionally, each nasal assembly comprises a nasal hood and an airtight elbow coupling for coupling the nasal hood to the filter.

Optionally, nasal hood comprises a one-way vent disposed in a side wall of the nasal hood.

In a fourth embodiment, the present invention is directed to a method of using the system, the method comprising the steps of: a) coupling the gas input to a gas source; b) securing a breathing apparatus to a face of each user; and c) turning on and distributing the gas flow to each of the breathing apparatuses.

DRAWINGS

These and other features, aspects, and advantages of the present invention will become better understood with reference to the following description, appended claims, and accompanying drawings where:

DESCRIPTION

As used herein, the following terms and variations thereof have the meanings given below, unless a different meaning is clearly intended by the contest in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

Figure 1:
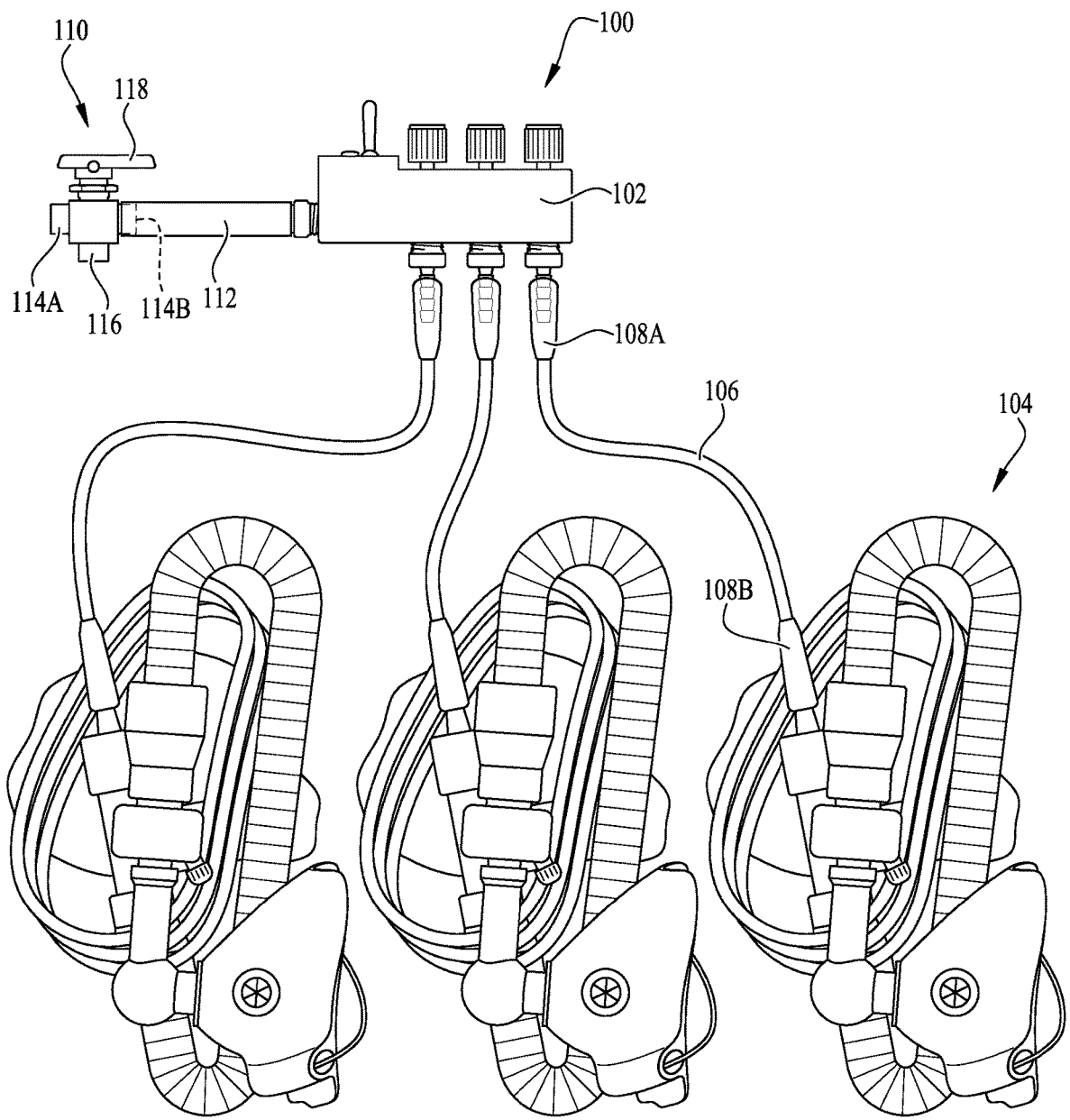
FIG. 1 is a top plan view of a breathing gas delivery system having features of the present invention.
Figure 2:
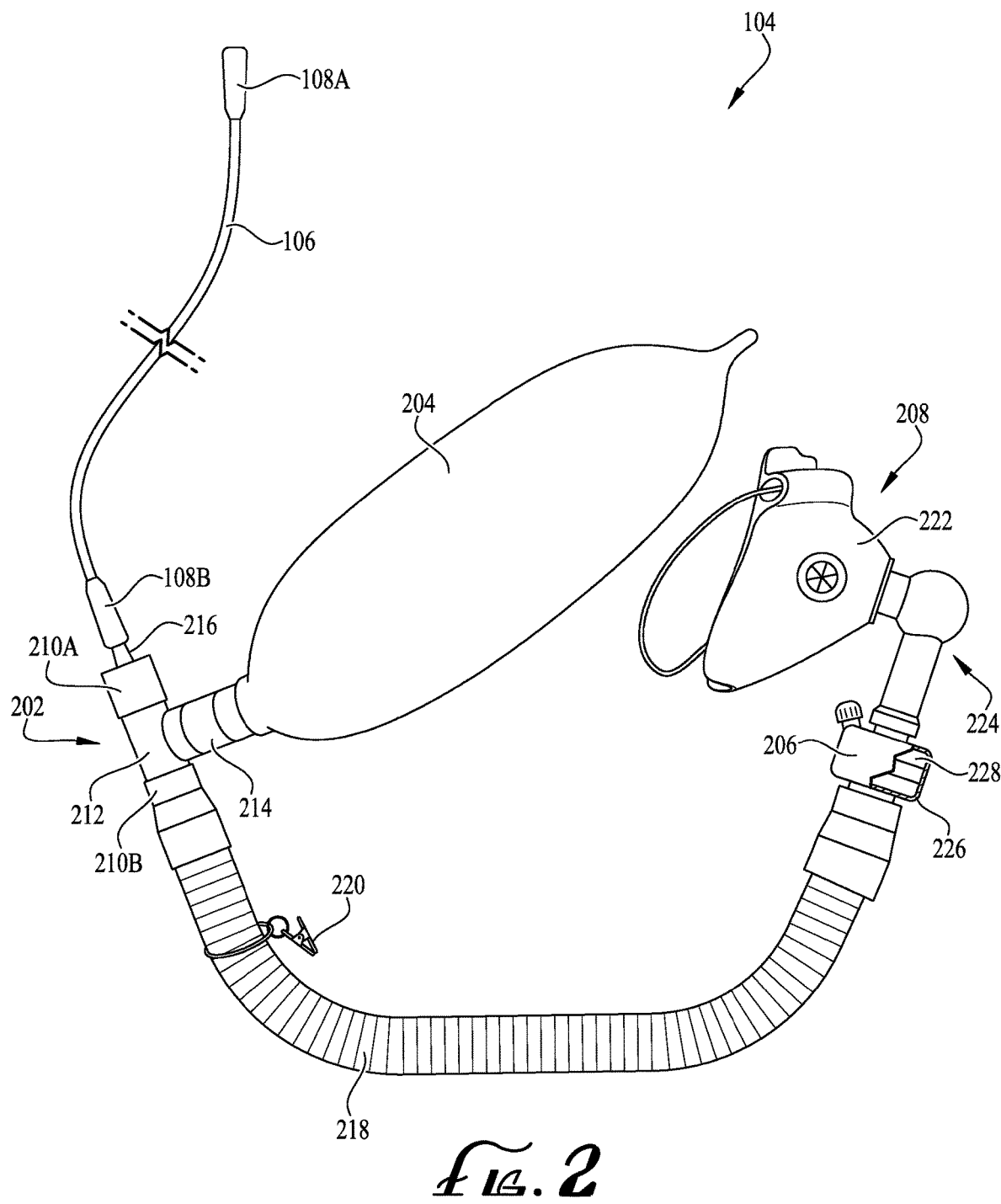
FIG. 2 is a top plan view of a first length of tubing and a breathing apparatus of FIG. 1.

Referring now FIGS. 1 and 2, there is shown a breathing gas delivery system 100 for use during removal of mercury dental fillings from a patient. The system 100 comprises a gas flow controller 102, at least one breathing apparatus 104 and at least one first length of tubing 106.

Referring now to FIGS. 3 through 7, the gas flow controller 102 has a body 302 with a longitudinal axis 402 extending along its length, an on/off switch/toggle 304, at least one gas input 306 and at least one gas output 308. The flow controller body 302 has a top surface 310, a bottom surface 312, two end surfaces 314A and 314B, and two side surfaces 316A and 316B.

Figure 3:
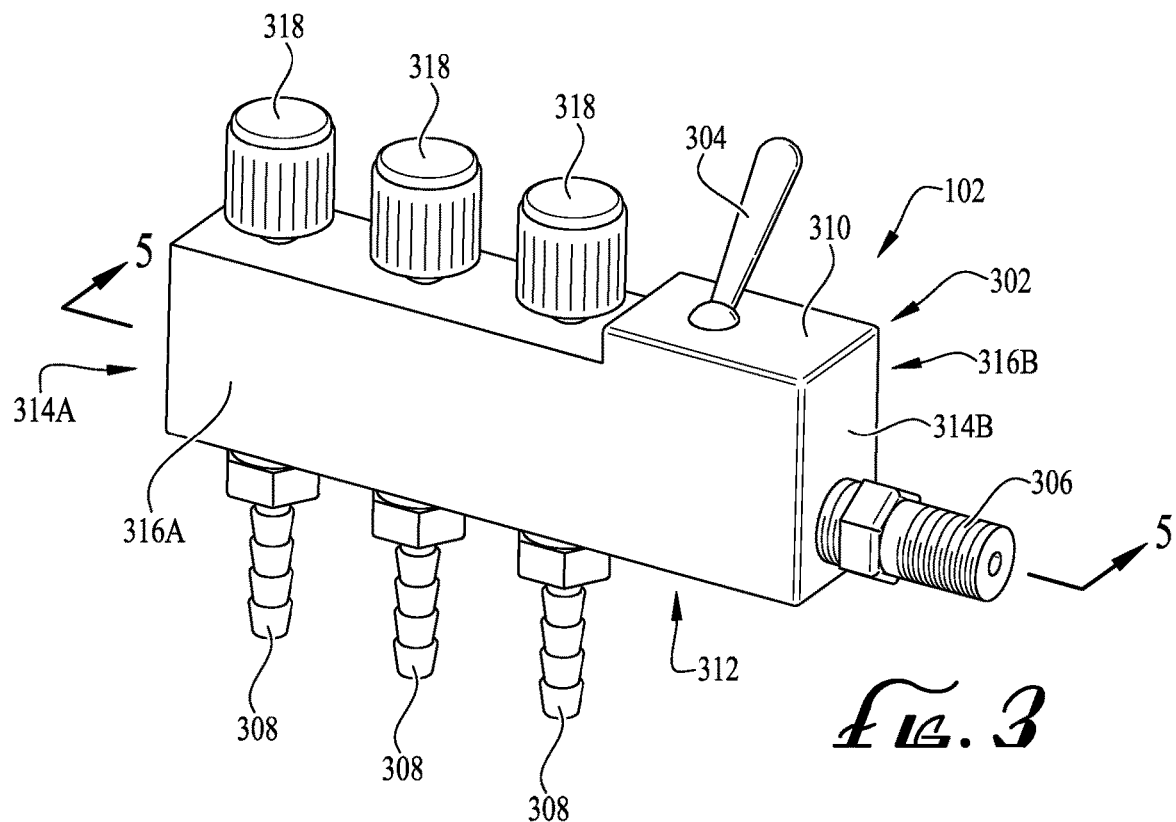
FIG. 3 is a perspective view of a flow controller according to FIG. 1.
Figure 4:
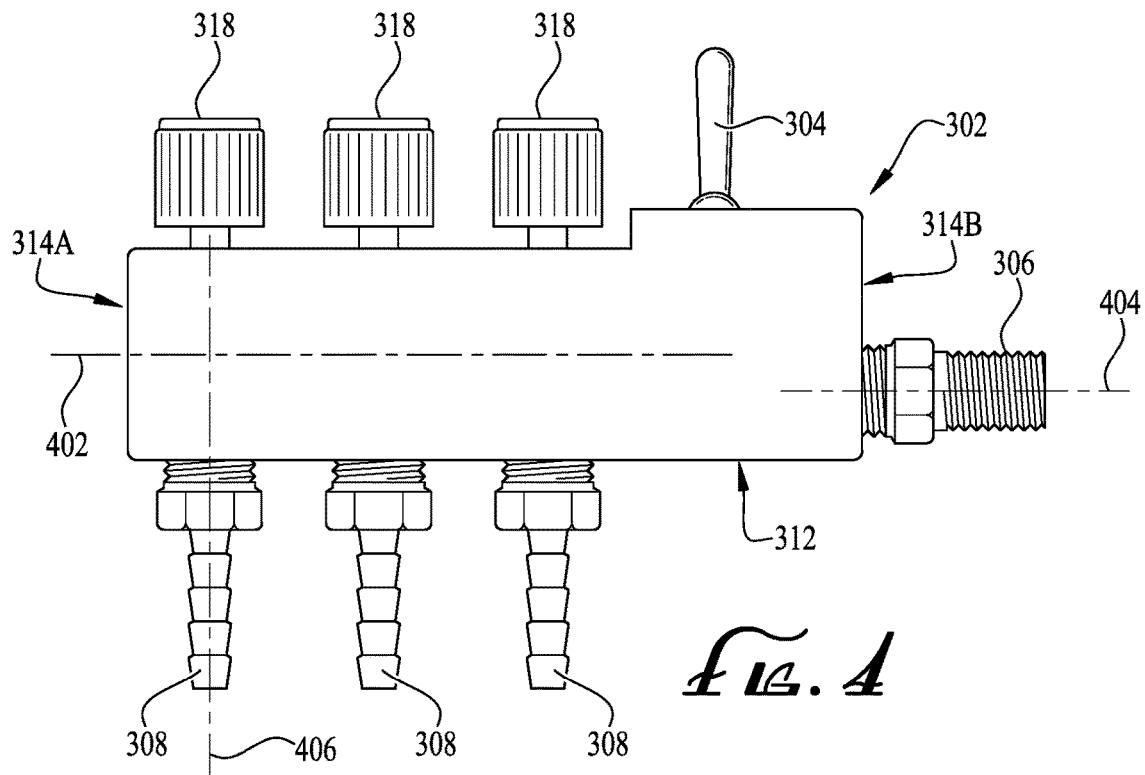
FIG. 4 is a side plan view of the flow controller of FIG. 3.
Figure 5:
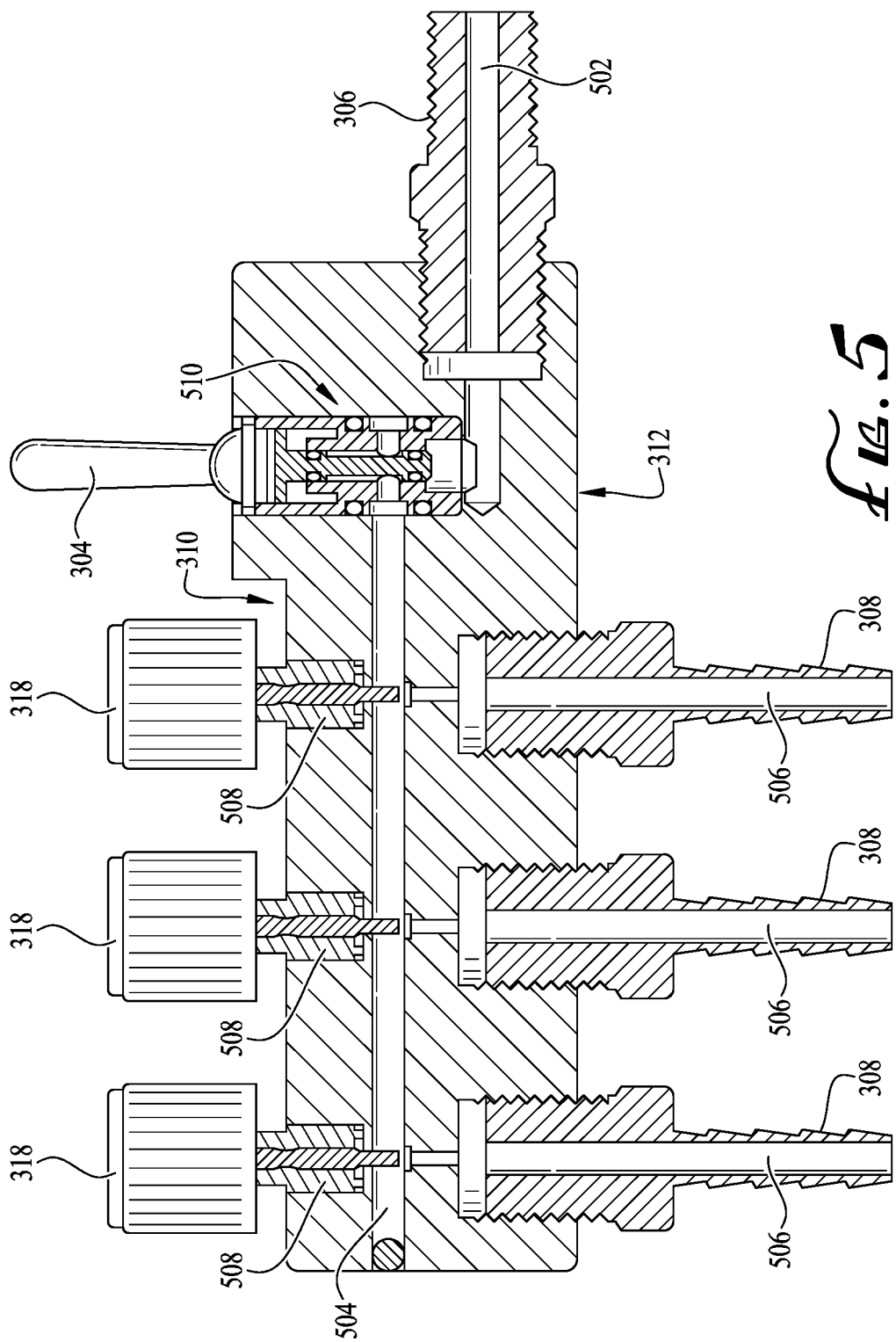
FIG. 5 is a sectional view of the flow controller of FIG. 3, taken along line 5-5.

Each gas input 306 comprises a longitudinal axis 404 extending along its length and each gas output 308 comprises a longitudinal axis 508 extending along its length. Preferably, there are three gas outputs 308 as shown in FIGS. 3 through 5. Typical dimensions of the body 302 are from about 1.0 inch to about 6 inches wide, from about 1.0 inch to about 6 inches long, and from about 1.0 inch to about 2.0 inches thick. The on/off switch/toggle 304 controls the breathing gas flow into the flow controller 102.

Figure 6:
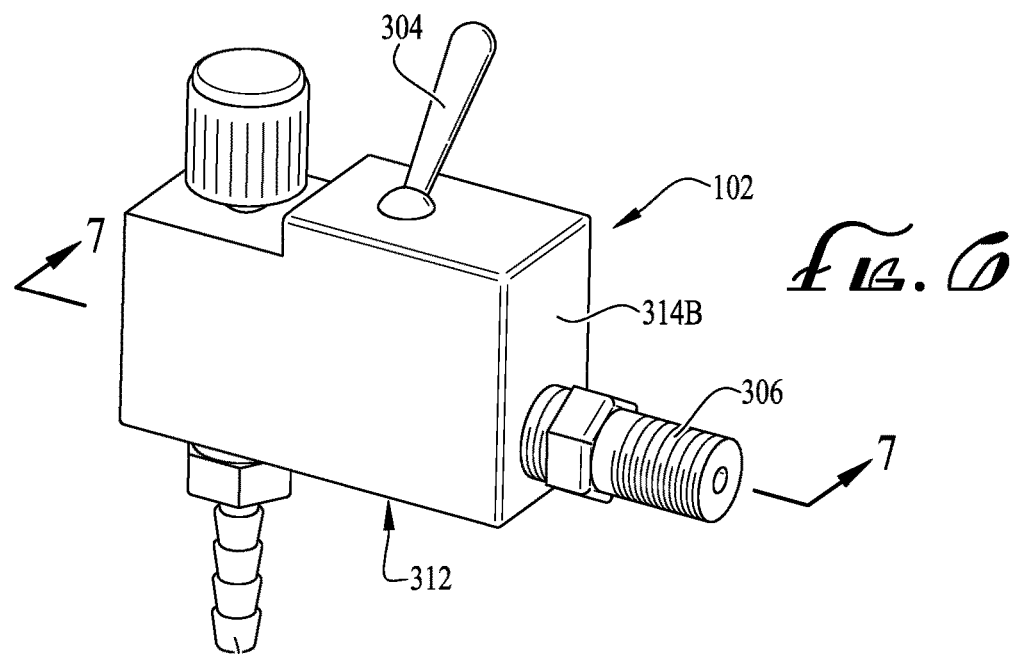
FIG. 6 is a perspective view of a flow controller having only one gas output.
Figure 7:
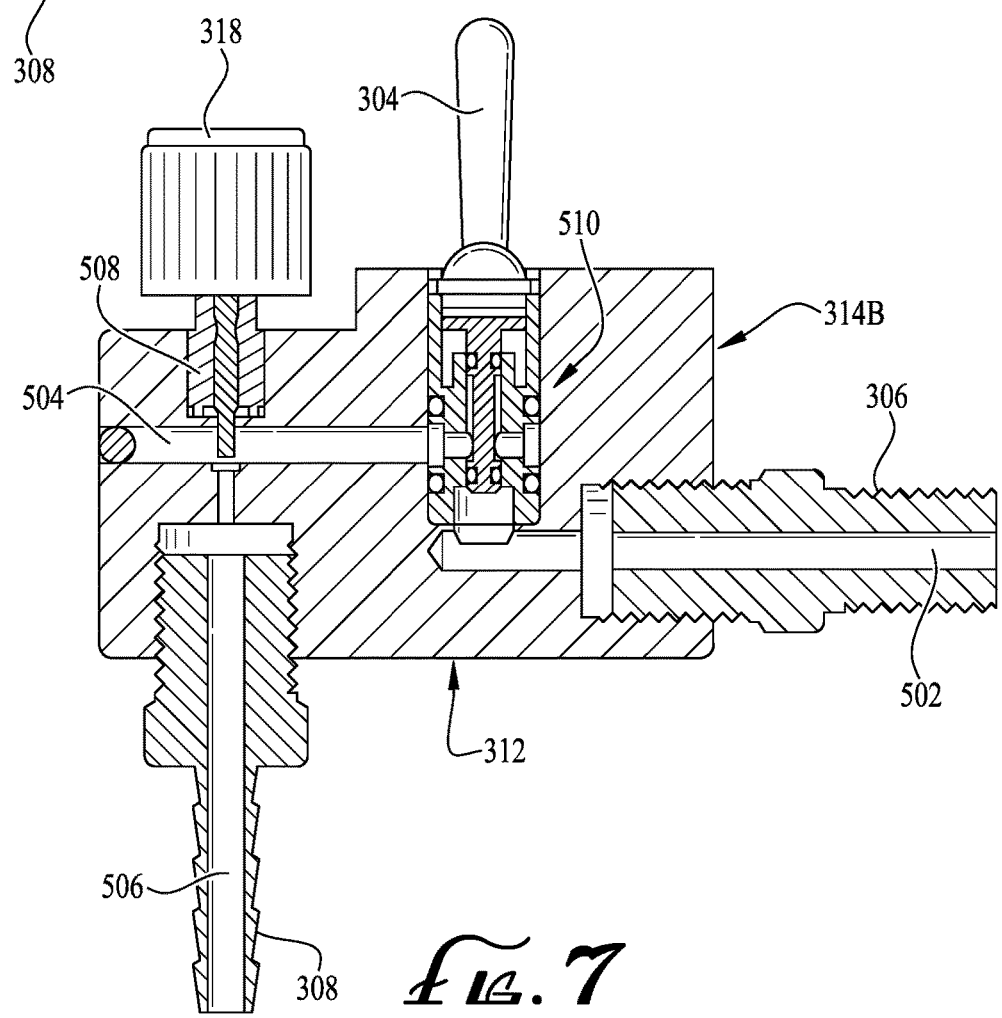
FIG. 7 is sectional view of the flow controller of FIG. 6, taken along line 7-7.

Optionally, as shown in FIGS. 6 and 7, the gas flow controller 102 can have one gas input 306 and one gas output 308. This configuration directs a one-way flow of breathing gas (oxygen) through the system. It was developed to allow singular usage by dentists who want their hygienist to have a non-contaminate breathing source while polishing teeth surfaces that encompass mercury amalgam fillings. The ambient air during this process has been assayed to have unsafe amounts of mercury vapor emanating from polishing these surface areas.

As best seen in FIGS. 5 and 7, the gas input 306 can be threadedly disposed within the end surface 314B of the flow controller body 302. Optionally, the gas input 306 is integrally formed with the body 302. The gas input 306 has a cylindrical gas input passageway 502 disposed there through that is in fluid communication with a single flow controller body passageway 504 disposed longitudinally through the flow controller body 302. The gas flowing into the gas input 306 must pass through the on/off switch mechanism 510 before the gas can enter the body passageway 504.

As shown in the Figures, the body passageway 504 intersects and is in fluid communication with cylindrical gas output passageways 506 disposed within the gas outputs 308, allowing for breathing gas to pass through the flow controller body 302 and into each gas output 308.

The longitudinal axis 404 of the gas input passageway 502 is parallel to the longitudinal axis 402 of the flow controller body 302 and is approximately perpendicular to the longitudinal axis' 406 of the gas output passageways 506. The gas input 306 can be ¼ inch in diameter and can comprise a threaded ¼-inch NPT adapter for coupling to a breathing gas source. The breathing gas source can either be an existing oxygen supply source such as a N2O/O2 inhalation sedation station, or an oxygen cylinder. An example of an acceptable gas input adapter 306 is made by Medical Support Products, having a place of business in Lancaster, Pa. Green oxygen seal tape, made from polytetrafluoroethylene film, manufactured by Taegatech, can be applied to the threads of the adapter 306 to ensure an airtight seal with the flow controller body 302. The green seal tape is ideal because it is designed to accommodate higher pressures. The gas input 306 can withstand an internal a pressure of 100 PSI (pounds per square inch).

As noted above, each gas output 308 comprises a passageway 506 with the longitudinal axis 406 approximately perpendicular to the longitudinal axis 402 of the flow controller body 302. Typically, if the body 302 has more than one gas output 308, the gas outputs 308 are spaced apart from each other from about 0.5 inches to about 2 inches, along the longitudinal axis of the flow controller body 302 and are threadedly disposed within the bottom surface 312 of the flow controller body 302. Optionally, the gas outputs 308 are integrally formed with the body 302, The gas output 308 can comprise an adapter, or manifold barb, threadedly disposed within the bottom surface 312 of the flow controller body 302 for coupling to the first length of tubing 106.

The first length of tubing 106 connects the gas output 308 to its respective breathing apparatus 104. Optionally, each gas output 308 typically comprises a ¼ inch NPT with a 3/16 inch or a ⅜ inch tube inside diameter output barb. An example of an acceptable gas output 308 manifold barb is made by Pneumadyne, having a place of business in Plymouth, Minn. White oxygen seal tape, made from polytetrafluoroethylene film, manufactured by Taegatech, can be applied to the threads of the adapters 308 to ensure an airtight seal with the flow controller body 302.

On the top surface 310 of the body 302, opposite each gas output 308, is a control mechanism 318 for independently regulating each gas output 308. As can be seen in FIGS. 3, 4, and 5, there are three control mechanisms 318, one for each gas output 308. As can be seen in FIGS. 6 and 7, there is one control mechanism 318 for controlling the one gas output 308. The control mechanism 318 can be a knob or dial coupled to a needle valve 508 that extends into the body passageway 504, and can cut off gas flow, or open gas flow, to the corresponding gas output 308. The needle valve 508 controls how much breathing gas is permitting to flow from the body passageway 504 to the gas output passageways 506.

Optionally, the flow controller body 302 can comprise a removable coupling system for removably coupling a surface. Preferably, the removable coupling system comprises hook and loop fasteners secured to the flow controller body 302 and the surface by adhesive. The surface can be a countertop, tabletop, or any other stable surface near the filling removal station. This allows the dentist or dental assistant to easily position the flow controller body 302 in any location desired.

As shown in FIG. 1, the system 100 can comprise at least one first length of tubing 106, depending on the number of individuals in the room that require protection from mercury inhalation. Preferably the system 100 comprises three first lengths of tubing 106, each first length of tubing 106 having two opposed ends 108A, 108B, where one end 108A is coupled to one of the gas outputs 308 of the flow controller body 302, and the other end 108B is coupled to a gas input 202 of a breathing apparatus 104.

Typically, each first length of tubing 106 can have a length of from about 12 inches to about 84 inches, a diameter of from about 3/16 inches to about ½ inch, and can be smooth bore or three-channel safety tubing made from flexible DEHP plastic, soft PVC plastic, vinyl, non-latex rubber or natural rubber latex. If the first length of tubing 106 is made from three-channel tubing, the three-channels help the tubing 106 resist kinks and occlusions. The tubing 106 also has no "memory" so it will remain straight when uncoiled, decreasing pull on cannulas and increasing overall comfort for the individuals wearing the breathing apparatuses 104. An example of an acceptable first length of tubing 106 is oxygen tubing sold by Salter Labs, having a place of business in Carlsbad, Calif.

As best seen in FIG. 2, the breathing apparatuses 104 each have a gas input 202, a breathing bag 204, a filter 206, and a nasal assembly 208. The gas input 202 is T-shaped, comprising two arms 210A, 210B that are coupled to and extend out perpendicularly from a body 212, the body 212 having a free end 214 not coupled to the arms 210A, 210B. The free end 214 of the body 212 is coupled to the breathing bag 204. One of the arms 210A is coupled by a tubing adapter 216 to the flow controller body 102 via the first length of tubing 106. The tubing adapter 216 can have an inside diameter of 21 mm and a length of 5-7 mm, tapering to one end. Optionally, the tubing adapter 216 can have a tapering length of from about 0.25 inches to about 2 inches. The other arm 210B is coupled to a second length of tubing 218 that connects to the filter 206. The arms 210A, 210B of the T-shaped gas input 202 (extending along the horizontal axis) have a 22 mm outside diameter, and the body 212 of the T-shaped gas input 202 (vertical axis) has 15 mm inside diameter and 22 mm outside diameter connection. Examples of an acceptable tubing adapter 216 and T-shaped gas input 202 are made by Hudson RCI (subsidiary of Teleflex), having a place of business in Morrisville, N.C.

The second length of tubing 218 is typically CPAP (continuous positive air pressure) tubing, with a smooth bore inner core and a crenelated outer surface to create a durable, flexible tube. The second length of tubing 218 is made from plastic or PVC (polyvinyl chloride), is re-usable and washable and has durable medical grade rubber endcaps that create a tight, long lasting seal with less cracking over time than older plastic products. An example of an acceptable second length of tubing 218 is sold by MVAP Medical Supplies, Inc., having a place of business in Newbury Park, Calif. Typically, each second length of tubing 218 can have a length of from about 12 inches to about 36 inches and an interior diameter of from about 10 mm to about 25 mm. Preferably the second length of tubing 218 has an interior diameter of about 19 mm, and each endcap has a diameter of 22 mm.

The breathing bag 204 can be made from a synthetic-rubber blend, neoprene, or latex. But preferably the breathing bag 204 is latex free. It can have a capacity of 0.5 to 3 liters, and can be in a barrel or 3-pleat slim design. An example of an acceptable breathing bag 204 is sold by Medline Industries, Inc., having a place of business in Illinois.

One or more breathing bag orientation clips 220 can be coupled to either the second length of tubing 218 or the T-shaped gas input 202 of the breathing apparatus 104 by a connector. The clips 220 allow the user to secure the second length of tubing 218 and/or breathing bag 204 to their clothing so that the breathing apparatus 104 is supported and does not pull downward on the user's face. An example of an acceptable clip 220 is sold by UMX Fashion Supplies, having a place of business in Walnut, Calif.

The filter 206 is a heat moisture exchanger and filters bacteria and viruses. The filter 206 comprises a housing 226 containing at least one layer of filter material 228. Preferably the filter housing 226 contains three layers of material 228, as shown in FIG. 2. The first two layers of material 228 are made from spun polypropylene with a calcium chloride coating, and the third layer 228 is made from an electrostatically charged filter media made of polypropylene and polyolefin plastic. The third layer 228 is hydrophobic and captures particles that measure between 0.3-10 microns in size. The electrostatic properties cause the third layer of material 228 to act like a magnet, helping it to attract both large and small particles into the filter's 206 pleated fabric. An example of an acceptable filter 206 is sold under the trade name ThermoFlo™ by ARC Medical, Inc., having a place of business in Tucker, Ga. The filter 206 can be located between the nasal assembly 208 and the second length of tubing 218, or optionally, between the second length of tubing 218 and the T-shaped gas input 202.

The nasal assembly 208 comprises a nasal hood 222 and an air-tight elbow coupling 224 which connects the hood 222 to the filter 206.

Figure 8:
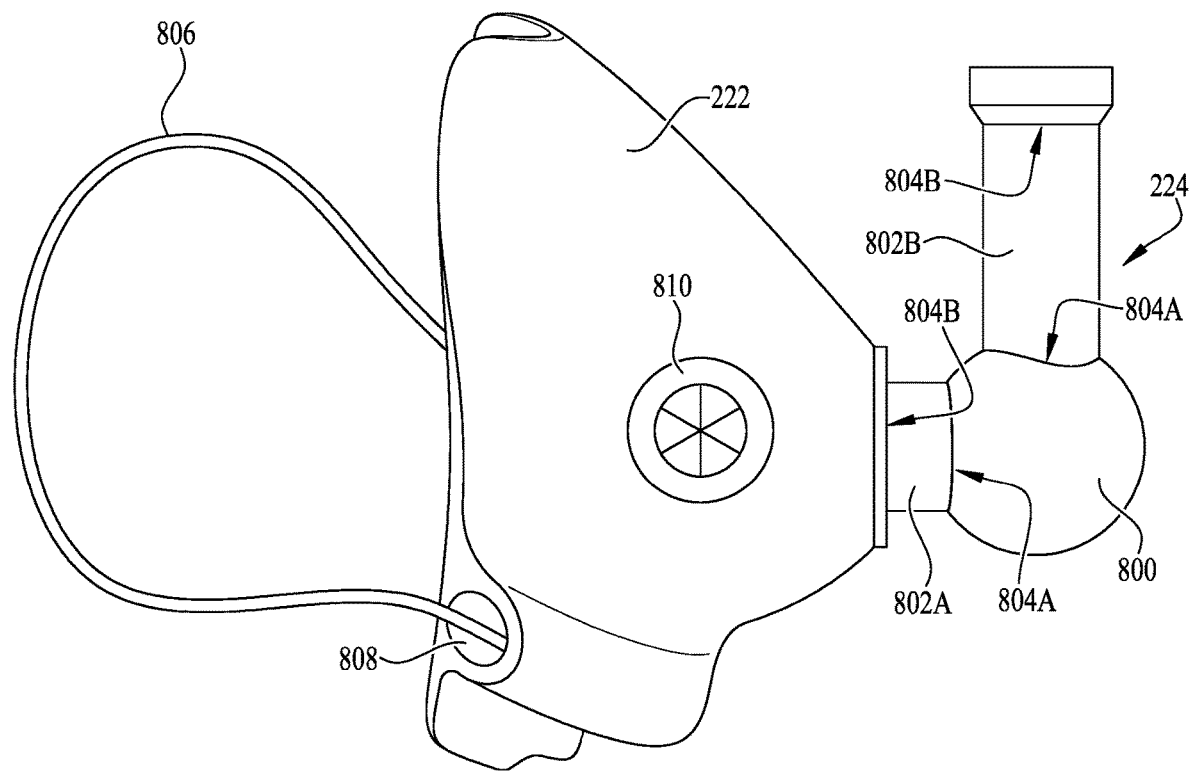
FIG. 8 is a side plan view of a nasal hood according to FIG. 1.
Figure 9:
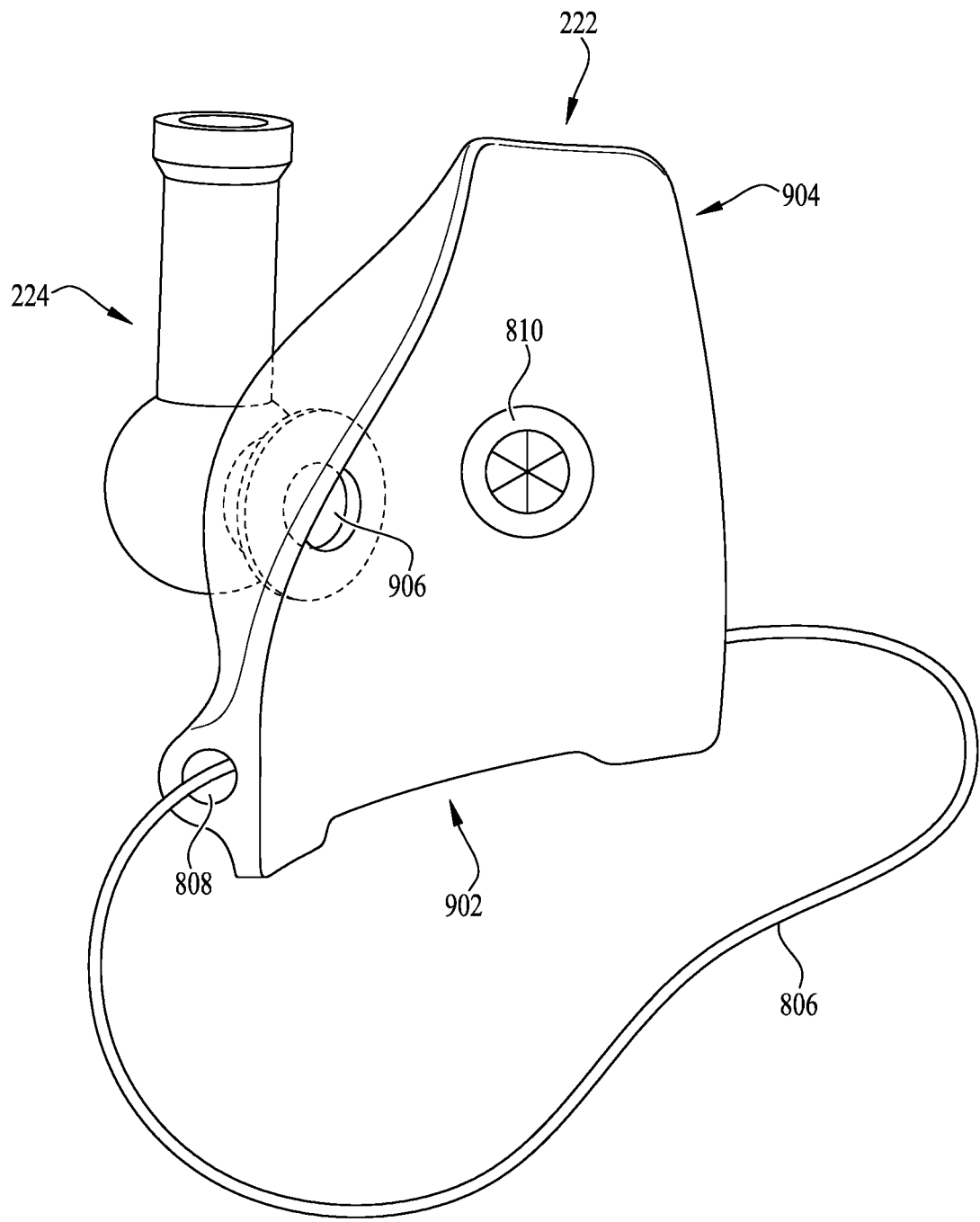
FIG. 9 is a perspective view of the nasal hood of FIG. 8, wherein an inside surface of the nasal hood is shown.

Referring now to FIGS. 8 and 9, the nasal hood 222 is shown. The nasal hood 222 can be made from natural or synthetic rubbers, thermoplastic elastomer (TPE), silicone or other plastics with or without plasticizers, and is roughly triangular in shape. The nasal hood 222 can be either rigid or flexible. The nasal hood 222 can have, but is not limited to, the following dimensions: an overall height of about 2 inches to about 4 inches, a base 902 having an approximate width of about 1.5 inches to about 2.5 inches (the base 902 being the portion of the nasal hood 222 proximate a user's lip when the nasal hood 222 is being worn), an apex 904 having an approximate width of about 0.5 inches to about 1.5 inches, and a depth of approximately 1 inch to about 2 inches (the depth being the distance a user's nose is able to project into the nasal hood). The nasal hood 222 also comprises a non-porous gasket insert that can be placed along a perimeter of the base 902 and the apex 904. The gasket insert is replaced for each patient.

The nasal hood 222 can comprise a one-way vent 810 disposed in a side wall of the nasal hood 222 to allow a user to exhale inhaled breathing gas. The one-way valve 810 does not allow outside air to pass through the vent 810 and into the nasal hood 22. Only exhaled air is able to pass out the nasal hood 222 through the vent 810.

The elbow coupling 224 can comprise a sphere 800 with two cylinders 802A, 802B extending from the sphere 800, creating an approximately 90 degree angled coupling. Each cylinder 802A, 802B has a proximal end 804A coupled to the sphere 800, and a free distal end 804B extending away from the sphere 800. One of the cylinders has two spaced apart flanges that extend around the perimeter of the free distal end. The two flanges help the elbow coupling to securely couple to the nose pillow assembly. The term "free" means "not fastened" to the sphere. The diameter of the cylinders is from about 0.5 inches to about 1.5 inches, but preferably the diameter is 1.0 inches.

The elbow coupling 224 can either be formed from a single piece of metal or plastic, or the elbow coupling 224 can be formed by bonding or joining the two cylinders 802A, 802B to the sphere 800. The sphere 800 and two cylinders 802A, 802B are hollow and in fluid communication with each other, such that breathing gas from the flow controller 102 can pass into the nasal hood 222 to be inhaled by the user.

Optionally, the elbow coupling 224 can comprise a single cylinder, bent at approximately a 90 degree angle. Optionally, the elbow coupling 224 can comprise a cube, with two cylinders extending therefrom. Thus, the elbow coupling 224 shape is not limited to what is described above.

As best seen in FIG. 9, there is an opening 906 disposed in the nasal hood 222 that the elbow coupling 224 is coupled to, permitting the elbow coupling 224 to dispense breathing gas into the nasal hood 222. It is important for the elbow coupling 224 to be of a solid, air-tight construction so that no ambient, mercury tainted air can leak into the breathing system 104 and be inhaled by the users. The elbow coupling 224 can be made from stainless steel or plastic, as long as the elbow coupling 224 is air-tight.

The nasal hood 222 can comprise one or more straps 806 to secure the nasal assembly 208 to the users' face. The straps 806 can be removably coupled to the nasal hood 222, or the straps 806 can be permanently coupled to the nasal hood 222.

If the straps 806 are permanently coupled, it is achieved by either permanent securing means such as clamps, rivets, glue, etc. or by being integrally formed with the nasal hood 222.

If the straps 806 are removably coupled, the straps 806 can be removably coupled by several means. For example, the each side of the nasal hood 222 can comprise a projection and one or both ends of the straps 806 can comprise an opening that fits over and secures to the projections on the nasal hood 222. Optionally, each of side of the nasal hood 222 can comprise an opening through which an end of the strap 806 threads. The threaded end of the strap 806 then loops back on itself, securing to itself by a clip, or hook and loop fashion. Optionally, each end of the straps 806 secure to the sides of the nasal hood 222 by clips, preferably alligator clips, that clip onto and grip the nasal hood 222. The one or more straps 806 can be adjustable, via a sliding mechanism, or buckle system, to accommodate different users head sizes. Optionally, the one or more straps 806 can be elastic, such that they automatically maintain the appropriate tension on the users face. Optionally, a single strap 806 is used that is threaded through an passageway 808 disposed along a bottom edge of the nasal hood 222.

In the event one strap 806 is used, the strap 806 couples to one side of the nasal hood 222, extends up over the users cheek, around the back of the users head, along the users other cheek, and couples to the other side of the nasal hood 222. In the event two straps 806 are used, one end of each strap 806 is coupled to one side of the nasal hood 222, and other ends of the straps 806 extend over the user's cheeks and secure to each other at the back of the users' head. The one or more straps 806 can have any shape, but preferably the straps are thin rectangles, optionally with rounded ends.

The system 100 can also comprise charcoal masks that are worn over the user's mouth(s) to help prevent any accidental inhalation of mercury fumes through their mouths.

As shown in FIG. 1, for those dentists who employ nitrous oxide/oxygen inhalation sedation, the system 100 can optionally comprise a 3-way T Port flow valve 110 that is attached to the oxygen inlet port of a nitrous oxide/oxygen inhalation sedation system flow meter, and coupled to the gas input 306 via a standard oxygen hose with female DISS connections at each end, should the patient require inhalation sedation. Due to the potential dental office variation of distances between the 3-way T Port flow valve 110 and the gas input 306 of the gas flow controller 102, custom oxygen hoses will need to be made for each purchaser exercising this option. For those dentists who do not employ the usage of nitrous oxide/oxygen inhalation sedation the valve 110 can be coupled directly to the gas input 306 via a standard oxygen hose with female DISS connections at each end. As stated above, due to the potential dental office variation of distances between the 3-way T Port flow valve 110 and the gas input 306 of the gas flow controller 102, custom oxygen hoses will need to be made for each purchaser exercising this option. The valve 110 has first arm 114A and a second arm 114B that extend longitudinally from each other, a body 116 that extends perpendicularly from the center of the two arms 114A, 114B, and a handle 118. The first arm 114A is coupled to the oxygen inlet port of an inhalation sedation system flow meter. The body 116 is coupled to an oxygen source.

The valve 110 has three different handle 118 positions, a first position, a second position, and a third position, and each handle 118 position corresponds to a different mode that the system 100 can operate in. The first position is longitudinally along the first arm 114A, the second position is longitudinally along the second arm 114B, and the third position is perpendicular to both the first and second arms 114A, 114B.

The three different modes are:

1) Inhalation sedation for patient alone during non-mercury removal procedures (handle position 1);

2) Oxygen breathing for patient, doctor and assistant during mercury removal procedures (handle position 2); and 3) Inhalation sedation for patient and oxygen to doctor and assistant during mercury removal procedures (handle position 3). In this position, the control mechanism 318 for the patient is closed by turning it clock-wise until it is closed. Oxygen will be supplied via the gas flow controller 102 solely to the doctor and assistant stations with this option.

In use, the system 100 provides a breathing gas simultaneously to the dentist performing the filling removal, the patient receiving the filling removal, and the dental assistant assisting in the filling removal. Because all individuals in the room receive a breathing gas via this airtight breathing system 100, there is a significantly reduced risk of inhaling any ambient mercury vapor. It should be noted that the system 100 only flows one way. Meaning, the breathing gas only flows through the system 100 in one direction, from the gas source via the flow controller 102 to the nasal hood 222, and into the user's nose. When the user wishes to exhale, they simply do so through their mouth. Optionally, the user can exhale through their nose, and the exhaled gas leaves the nasal hood 222 via the one-way valve 810. The user does not exhale through their nose, and back into the system 100. It is not possible due to the positive pressure flow of the breathing gas.

The first step of using the system 100 requires coupling the flow controller body 102 to a breathing gas source. Typically, the breathing gas source is an oxygen tank. Next, the patent, dentist, and dental assistant each secure a breathing assembly 104 to their faces. Once all three breathing assemblies 104 are secured to their respective user, the flow controller 102 is turned on via the on/off switch 304, and the flow of breathing gas to each breathing assembly 104 is adjusted via the control mechanism 318 to an appropriate level. Once breathing gas is flowing to the three breathing assemblies 104, the removal of the mercury filling can commence.

The present invention has the following advantages:

1) Currently, there is no comprehensive breathing gas system for use during removal of mercury fillings. Current standard practice for removal of mercury fillings involves using a standard nitrous oxide/oxygen facemask on the patient, and respirator masks on the dentist and dental assistant. The nitrous oxide masks are quite too bulky and may do not form an airtight seal with the patient, therefore leaking in ambient air. Also, the dual supply tubes that are tightened at the back of the dental chair disallow patient head rotation, which is a restrictive factor in removing mercury fillings. The respirator masks for doctor and assistant may be effective in preventing the introduction of mercury vapor, but are claustrophobic, bulky, difficult to place, adjust and remove, and can interfere with dental magnifying glasses that most all dentists use. The present invention provides an airtight breathing gas delivery system for the patient, dentist and dental assistant, so that all three persons can breathe clean oxygen without fear of inhaling dangerous mercury vapors;

2) The nasal assembly of the present invention is low profile and does not block the patients mouth—providing ease of access to the mouth for the dentist;

3) The nasal assembly and straps are made from soft, flexible material such as silicone so that it is comfortable to wear during the filling removal;

4) Maximum comfort—less than 2 ounces in weight;

5) Ease of placement and removal with head strap attachments;

6) Effective nasal insert elements seal with users nares and prohibit introduction of ambient air;

7) Clarity of communication between doctor and assistant compared to the muffled voicing inherent with respirator masks;

8) Effective disinfection, filtration and maintenance,

9) Removable in-line disposable filter element to assure no internal bacterial contamination of tube and bag assemblies;

10) Rotation of patient's head to better access operative sites compared to the restricted lateral movements of nitrous oxide/oxygen nasal hoods with dual tubes that cinch the patient's head to the dental chair;

11) Ease of breathing, as the breathing bag is less than 2 feet from the nasal assembly rather than at the remote flowmeter oxygen supply source common with N2O/O2 inhalation sedation systems; and 12) An emergency oxygen system for the patient.

Although the invention has been described in terms of a preferred embodiment, nevertheless, changes and modifications can be made which do not depart from the spirit, scope and teachings of the invention. Such changes and modifications are deemed to fall within the purview of the present invention as claimed.

What is claimed is:

1. A breathing gas delivery system comprising:
   a) a gas flow controller, the gas flow controller comprising a body having:
      i) an on/off switch coupled to the body for controlling breathing gas flow into the flow controller;
      ii) a body passageway disposed through the body;
      iii) at least one gas input disposed within the body, the gas input comprising a gas input passageway disposed there through, the gas input passageway being in fluid communication with the body passageway;
      iv) three gas outputs disposed within the body, each gas output comprising a gas output passageway disposed there through, each gas output passageway being in fluid communication with the body passageway and the gas input passageway; and
      v) three control mechanisms disposed along the body, where each control mechanism corresponds to and controls one of the three gas outputs;
   b) three breathing apparatuses, each breathing apparatus comprising:
      i) a T-shaped gas input having two arms coupled to and extending perpendicularly to a body, the body having a free end;
      ii) a breathing bag coupled to the free end of the body of the T-shaped gas input;
      iii) a second length of tubing having two opposed ends, wherein one end is coupled to a first of the two arms of the T-shaped gas input;
      iv) a filter containing at least one layer of material coupled to the other end of the second length of tubing; and
      v) a nasal assembly coupled to the filter; and
   c) three first lengths of tubing coupling the breathing apparatuses to the gas flow controller, each first length of tubing having two opposed ends, wherein one end is coupled to a respective one of the breathing apparatuses and the other end is coupled to a respective one of the gas outputs.

2. The system of claim 1, wherein the control mechanisms each comprise a dial coupled to a needle valve that extends into the body passageway and controls flow of gas to the corresponding gas output.

3. The system of claim 1, wherein the nasal assembly comprises a nasal hood.

4. The system of claim 3, wherein the nasal hood comprises a one-way vent disposed in a side wall of the nasal hood.

5. The system of claim 1, wherein the nasal assembly comprises a nasal hood and an airtight elbow coupling for coupling the nasal hood to the filter.

6. The system of claim 5, wherein the elbow coupling comprises a sphere with two cylinders extending from the sphere.

7. A method of using the system of claim 1, the method comprising the steps of:
   a) coupling the gas input to a gas source;
   b) securing a respective one of the breathing apparatuses to a face of each user; and
   c) turning on gas flow to the breathing apparatuses.

8. A breathing gas delivery system comprising:
   a) a gas flow controller comprising a body having:
      i) an on/off switch;
      ii) at least one gas input; and
      iii) three gas outputs;
   b) three breathing apparatuses, wherein each breathing apparatus comprises:
      i) a T-shaped gas input having a body with two arms and a free end;
      ii) a breathing bag coupled to the free end of the body of the T-shaped gas input;
      iii) a second length of tubing having two opposed ends, wherein one end is coupled to a first of the two arms of the respective T-shaped gas input;
      iv) a filter coupled to the other end of the second length of tubing; and
      v) a nasal assembly coupled to the filter; and
   c) three first lengths of tubing coupling the breathing apparatuses to the gas flow controller, each first length of tubing having two opposed ends, wherein one end is coupled to a respective one of the breathing apparatuses and the other end is coupled to a respective one of the gas outputs.

9. The system of claim 8, wherein each nasal assembly comprises a nasal hood.

10. The system of claim 9, wherein each nasal hood comprises a one-way vent disposed in a side wall of the nasal hood.

11. The system of claim 8, wherein each nasal assembly comprises a nasal hood and an airtight elbow coupling for coupling the nasal hood to the respective filter.

12. The system of claim 11, wherein the elbow coupling comprises a sphere with two cylinders extending from the sphere.

13. A method of using the system of claim 8, the method comprising the steps of:
   a) coupling the gas input to a gas source;
   b) securing a respective one of the breathing apparatuses to a face of a user; and
   c) turning on gas flow to the breathing apparatus.

* * * * *